United States Patent [19]
Rosenberger et al.

[11] 3,948,854
[45] Apr. 6, 1976

[54] SALICYLIC ACID HYDRAZIDE STABILIZERS FOR POLYMERS

[75] Inventors: Siegfried Rosenberger, Riehen; Kurt Schwarzenbach, Pfeffingen, both of Switzerland

[73] Assignee: Ciba-Geigy Corporation, Ardsley, N.Y.

[22] Filed: May 8, 1975

[21] Appl. No.: 575,669

[30] Foreign Application Priority Data
May 16, 1974 Switzerland.......................... 6720/74

[52] U.S. Cl...................... 260/45.85 A; 260/471 C
[51] Int. Cl.²............................................ C08J 3/20
[58] Field of Search................ 260/45.85 A, 471 C

[56] References Cited
UNITED STATES PATENTS

| | | | |
|---|---|---|---|
| 3,260,740 | 7/1966 | Crowther et al. | 260/471 C |
| 3,509,093 | 4/1970 | Lehmann et al. | 260/45.85 A |

FOREIGN PATENTS OR APPLICATIONS
1,150,391   6/1963   Germany

OTHER PUBLICATIONS
Journal of Heterocyclic Chemistry – 2 (1); 37 to 40, 1965

*Primary Examiner*—V. P. Hoke
*Attorney, Agent, or Firm*—Charles W. Vanecek

[57] ABSTRACT
Compounds of the formula

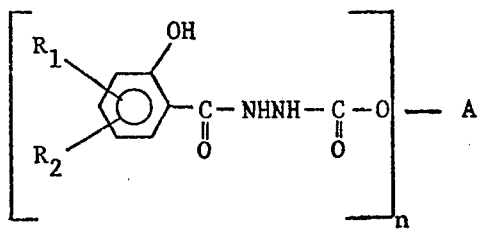

in which $R_1$ denotes hydrogen, alkyl with 1–8 carbon atoms, alkenyl with 3 or 4 carbon atoms, cycloalkyl with 5–8 carbon atoms, aralkyl with 7–9 carbon atoms, phenyl, chlorine, bromine, hydroxyl, alkoxy with 1–18 carbon atoms or acyloxy with 2–18 carbon atoms, $R_2$ denotes hydrogen, alkyl with 1–5 carbon atoms, alkenyl with 3 or 4 carbon atoms, cyclohexyl, aralkyl with 7–9 carbon atoms, chlorine or bromine, $n$ denotes 1 and A denotes alkyl with 1–21 carbon atoms, alkenyl with 3–6 carbon atoms, alkynyl with 3–6 carbon atoms, oxaalkyl with 2–21 carbon atoms, thiaalkyl with 2–21 carbon atoms, the hetero-atoms in the oxaalkyl or thiaalkyl radical being separated from one another and/or from the oxygen atom to which these radicals are bonded, by at least 2 carbon atoms, cyclohexyl or benzyl, or $n$ denotes 2 and A denotes alkylene with 2–10 carbon atoms, alkenylene with 4 carbon atoms, alkynylene with 4 carbon atoms, oxaalkylene with 4–10 carbon atoms or thiaalkylene with 4–10 carbon atoms, the hetero-atoms in the oxaalkylene or thiaalkylene radical being separated from one another and/or from the oxygen atom to which these radicals are bonded, by at least 2 carbon atoms, can be used for stabilising organic material, especially in the presence of metals.

7 Claims, No Drawings

SALICYLIC ACID HYDRAZIDE STABILIZERS FOR POLYMERS

The subject of the present invention are salicyloylhydrazinecarboxylic acid esters and their use for stabilising organic materials.

The present invention relates to the use of the compounds of the formula I

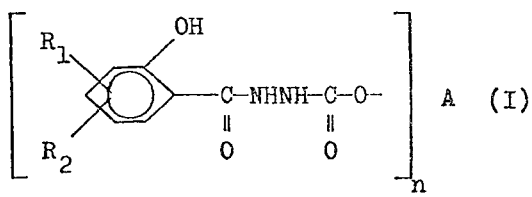

in which $R_1$ denotes hydrogen, alkyl with 1-8 carbon atoms, alkenyl with 3 or 4 carbon atoms, cycloalkyl with 5-8 carbon atoms, aralkyl with 7-9 carbon atoms, phenyl, chlorine, bromine, hydroxyl, alkoxy with 1-18 carbon atoms or acyloxy with 2-18 carbon atoms, $R_2$ denotes hydrogen, alkyl with 1-5 carbon atoms, alkenyl with 3 or 4 carbon atoms, cyclohexyl, aralkyl with 7-9 carbon atoms, chlorine or bromine, n denotes 1 and A denotes alkyl with 1-21 carbon atoms, alkenyl with 3-6 carbon atoms, alkynyl with 3-6 carbon atoms, oxaalkyl with 2-21 carbon atoms, thiaalkyl with 2-21 carbon atoms, the hetero-atoms in the oxaalkyl or thiaalkyl radical being separated from one another and/or from the oxygen atom, to which these radicals are bonded, by at least 2 carbon atoms, cyclohexyl or benzyl or n denotes 2 and A denotes alkylene with 2-10 carbon atoms, alkenylene with 4 carbon atoms, alkynylene with 4 carbon atoms, oxaalkylene with 4-10 carbon atoms or thiaalkylene with 4-10 carbon atoms, the hetero-atoms in the oxaalkylene or thiaalkylene radical being separated from one another and/or from the oxygen atoms, to which these radicals are bonded, by at least 2 carbon atoms, for stabilising organic material, especially in the presence of metals.

These compounds are new, with the exception of β-carbethoxysalicyloyl-hydrazide, which has been described in J. Heterocyclic Chem. 2 (1), 37 (1965).

Preferred compounds of the formula I are those in which $R_1$ denotes hydrogen, hydroxyl, chlorine or alkoxy with 1-18 carbon atoms, $R_2$ denotes hydrogen, n denotes 1 and A denotes alkyl with 2-18, preferably 3-18, and particularly preferentially 8-18, carbon atoms, or benzyl, or n denotes 2 and A denotes alkylene with 6 carbon atoms, alkenylene with 4 carbon atoms, alkynylene with 4 carbon atoms, oxaalkylene with 4-10 carbon atoms ro thiaalkylene with 4-10 carbon atoms, the hetero-atoms in the oxaalkylene or thiaalkylene radical being separated from one another and/or from the oxygen atoms, to which these radicals are bonded, by at least 2 carbon atoms.

The compounds of the formula I are not only excellent stabilisers, particularly metal deactivators, but in addition have the advantage that in contrast to similar previously known compounds they are odourless when used in fats, oils and waxes, and that in polyolefines they show improved compatibility with the substrate.

If $R_1$, $R_2$ and/or A in the formula I represent alkyl groups, these can be, within the scope of the stated limits, methyl, ethyl, propyl, iso-propyl, butyl, sec.-butyl, tert.-butyl, amyl, tert.-amyl, sec.-amyl, hexyl, iso-heptyl, octyl, tert.-octyl, nonyl, dodecyl, tetradecyl, hexadecyl, octa-decyl or eicosyl. If $R_1$ and/or $R_2$ are alkenyl groups, they can be allyl or butenyl.

$R_1$ can be a cycloalkyl group with 5-8 carbon atoms such as, for example, cyclohexyl, α-methylcyclohexyl or cyclo-octyl. If $R_1$ and/or $R_2$ are aralkyl groups, these can be benzyl or α-phenylethyl.

If $R_1$ is an alkoxy group with 1-18 carbon atoms, it can be, for example, methoxy, ethoxy, propoxy, butoxy, hexoxy, octoxy, decyloxy, dodecyloxy, tetradecyloxy or octadecyloxy. $R_1$ can also denote an acyloxy group with 2-18 carbon atoms, in which "acyl" can be, for example, the acyl radicals of the following acids: acetic acid, propionic acid, butyric acid, isobutyric acid, valeric acid, caproic acid, 2-ethylcaproic acid, caprylic acid, capric acid, lauric acid, myristic acid, palmitic acid, stearic acid, acrylic acid, methacrylic acid, crotonic acid, oleic acid, benzoic acid, phenylacetic acid and salicylic acid.

If A denotes alkenyl with 3-6 carbon atoms, it can be propenyl, butenyl, pentenyl or hexenyl.

If A denotes alkynyl with 3-6 carbon atoms, it can be, for example, propargyl.

If A denotes oxaalkyl with 2-21 carbon atoms it can denote, for example, 3-oxabutyl, 3-oxapentyl, 3-oxaheptyl, 3-oxapentadecyl or 3-oxaheneicosyl, and if A denotes thiaalkyl with 2-21 carbon atoms it can denote, for example, 3-thiabutyl, 3-thiapentyl, 3-thiaheptyl, 3-thiaundecyl, 3-thiapentadecyl, 3-thianonadecyl and 3-thiaheneicosyl.

If A in the definition of the formula I is alkylene with 2-10 carbon atoms, it can be, for example, ethylene, propylene, trimethylene, tetramethylene, 2,2-dimethylpropylene, hexamethylene, octamethylene or decamethylene.

If A denotes alkenylene or alkynylene each with 4 carbon atoms, it can be butenylene or butynylene.

A as oxaalkylene with 4-10 carbon atoms can denote the divalent radical of 3-oxapentane, 3-oxaheptane or 3-oxadecane whilst A as thiaalkylene with 4-10 carbon atoms can denote the divalent radical of 3-thiapentane, 3-thiaheptane or 3-thiadecane.

Examples of compounds of the formula I are: N-salicyloyl-hydrazinecarboxylic acid methyl ester, N-salicyloyl-hydrazinecarboxylic acid octyl ester, N-salicyloyl-hydrazinecarboxylic acid octadecyl ester, N-salicyloyl-hydrazinecarboxylic acid benzyl ester, N-(5-chloro-2-hydroxy-benzoyl)-hydrazinecarboxylic acid ethyl ester, N-(2,5-dihydroxy-benzoyl)-hydrazinecarboxylic acid ethyl ester, N-(4-methoxy-2-hydroxy-benzoyl)-hydrazinecarboxylic acid ethyl ester, N-(5-cyclohexyl-2-hydroxybenzoyl)-hydrazinecarboxylic acid ethyl ester, N-(4-acetoxy-2-hydroxy-benzoyl)-hydrazinecarboxylic acid ethyl ester, N-(3,5-di-t-butyl-2-hydroxy-benzoyl)-hydrazinecarboxylic acid ethyl ester, the hexanediol ester of N-salicyloyl-hydrazinecarboxylic acid, the diethylene glycol diester of N-salicyloyl-hydrazinecarboxylic acid and the thiodiethylene glycol diester of N-salicyloyl hydrazinecarboxylic acid.

The compounds of the formula I can be manufactured by two reaction methods which are in theselves known:

a. Reaction of equimolar amounts of a salicylic acid hydrazide of the general formula

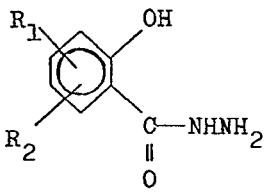

and a chloroformic acid ester of the general formula

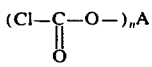

in the presence of a tert.-amine or of an inorganic base, in a solvent or without solvents.

Preferred amines are triethylamine and pyridine and preferred inorganic bases are alkali metal hydroxides, alkali metal carbonates and alkali metal bicarbonates. Solvents which can be used are those which are inert towards the acid chlorides, preferably aromatics such as benzene or toluene and xylene, esters such as diethyl ether, dioxane and ethylene glycol dimethyl ether, acetonitrile, amides such as dimethylacetamide, tetramethylurea and tert.-amines such as pyridine and triethylamine.

b. Reaction of equimolar amounts of a hydrazinecarboxylic acid ester of the general formula

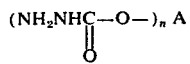

and of a salicyloyl chloride of the general formula

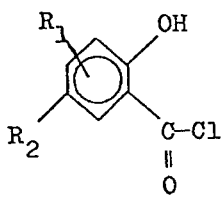

under the conditions mentioned under (a).

The compounds of the formula I are used as stabilisers for organic substrates, such as:

1. Fats, oils and waxes which are pure monomeric compounds or mixtures of such compounds, for example lubricating oils, mineral oils, animal and vegetable fats, oils and waxes, or oils, waxes and fats based on synthetic esters as well as mixtures of synthetic esters with mineral oils in any desired weight ratios.

2. Polyolefines, for example polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene/propylene copolymers, propylene/butene-1 copolymers, propylene/isobutylene copolymers and styrene/butadiene copolymers, as well as terpolymers of ethylene and propylene with a diene such as, for example, hexadiene, dicyclopentadiene or ethylidenenorbornene, and mixtures of the abovementioned homopolymers, such as, for example, mixtures of polypropylene and polyethylene, polypropylene and polybutene-1, or polypropylene and polyisobutylene.

The compounds of the formula I are incorporated into the substrate in a concentration of 0.005 to 5% by weight, calculated relative to the material to be stabilised.

Preferably, 0.01 to 1.0, and particularly preferentially 0.02 to 0.5, % by weight of the compounds, calculated relative to the material to be stabilised, are incorporated into the material. They can be incorporated, for example, by mixing in at least one of the compounds of the formula I and, optionally further additives, in accordance with methods customary in the art, in the case of polyolefines also before or during moulding, or by applying the dissolved or dispersed compounds to the polyolefine, if appropriate with subsequent evaporation of the solvent.

In the case of crosslinked polyethylene, the compounds are added before crosslinking.

The compounds of the formula I can also be added before or during polymerisation, and where they can be built into the polymer chain it is possible to obtain stabilised substrates in which the stabilisers are not volatile or extractable.

The following should be mentioned as examples of further additives together with which the stabilisers can be employed:

1. ANTIOXIDANTS 1.1. Simple 2,6-dialkylphenols such as, for example, 2,6-di-tert.butyl-4-methylphenol, 2-tert.butyl-4,6-dimethyl-phenol, 2,6-di-tert.butyl-4-methoxymethylphenol and 2,6-dioctadecyl-4-methylphenol.

1.2. Derivatives of alkylated hydroquinones such as, for example, 2,5-di-tert.butyl-hydroquinone, 2,5-di-tert.amylhydroquinone, 2,6-di-tert.butyl-hydroquinone, 2,5-di-tert.butyl-4-hydroxy-anisole, 3,5-di-tert-.butyl-4-hydroxy-anisole, tris-(3,5-di-tert.butyl-4-hydroxyphenyl)-phosphite, 3,5-di-tert.butyl-4-hydroxyphenyl-stearate and bis-(3,5-di-tert.butyl-4-hydroxyphenyl)-adipate.

1.3. Hydroxylated thiodiphenyl ethers such as, for example, 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol), 4,4'-thio-bis-(6-tert.butyl-2-methylphenol) and 4,4'-bis-(2,6-di-methyl-4-hydroxyphenyl)-disulphide.

1.4. Alkylidene-bisphenols such as, for example, 2,2'-methylene-bis-(6-tert.butyl-4-methylphenol), 2,2'-methylene-bis-(6-tert.butyl-4-ethylphenol), 4,4'-methylene-bis-(6-tert.-butyl-2-methylphenol), 4,4'-methylene-bis-(2,6-di-tert.butyl-phenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.butyl-4-hydroxy-2-methylphenyl)-4-n-dodecylmercapto-butane, 1,1,5,5-tetra-(5-tert.butyl-4-hydroxy-2-methylphenyl)-pentane and ethylene-glycol-bis-[3,3-bis-(3'-tert.butyl-4'-hydroxyphenyl)-butyrate].

1.5. O-, N- and S-benzyl compounds such as, for example, 3,5,3',5'-tetra-tert.butyl-4,4'-dihydroxydibenzyl ether, 4-hydroxy-3,5-dimethylbenzyl-mercaptoacetic acid octadecyl ester, tri-(3,5-di-tert.butyl-4-hydroxybenzyl)-amine and bis-(4-tert.butyl-3-hydroxy-2,6-dimethylbenzyl)-dithio-terephthalate.

1.6. Hydroxybenzylated malonic esters such as, for example, 2,2-bis-(3,5-di-tert.butyl-2-hydroxybenzyl)-malonic acid dioctadecyl ester, 2-(3-tert.butyl-4-hydroxy-5-methyl-benzyl)-malonic acid dioctadecyl ester, 2,2-bis-(3,5-di-tert.butyl-4-hydroxybenzyl)-malonic acid didodecylmercapto ethyl ester and 2,2-bis-(3,5-di-tert.butyl-4-hydroxybenzyl)-malonic acid di-[4-(1,1,3,3-tetramethylbutyl)-phenyl] ester.

1.7 Hydroxybenzyl-aromatics such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenxyl)-phenol.

1.8. s-Triazine compounds such as for example 2,4-bis-octylmercapto-6-(3,5-di-tert.butyl-4 -hydroxyanilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.buty-4-hydroxybenzyl)-isocyanurate.

1.9. Amides of β-(3,5-di-tert.butyl-4-hydroxyphenyl)-propionic acid such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl-hexamethylenediamine.

1.10 Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]-octane.

1.11. Esters of β-(5-tert.butyl-4-hydroxy-3-methylphenyl)-propionic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, trishydroxyethylisocyanurate and 4-hydroxymethyl-1-phospha-2,6,7-trioxabicyclo-[2,2,2]-octane.

1.12. Esters of 3,5-di-tert.butyl-4-hydroxyphenylacetic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo-[2,2,2]-octane.

1.13. Acylaminophenols such as, for example, N-(3,5-di-tert.butyl-4-hydroxyphenyl)-stearic acid amide and N,N'-di-(3,5-di-tert.butyl-4-hydroxyphenyl)-thio-bis-acetamide.

1.14. Benzylphosphonates such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example phenyl-1-naphthylamine, phenyl-2-naphthylamine, N,N'-di-phenyl-p-phenylenediamine, N,N'-di-2-naphthyl-p-phenylenediamine, N,N'-di-2-naphthyl-p-phenylenediamine, N,N'-di-sec.butyl-p-phenyl-enediamine, 6-ethoxy-2,2,4-trimethyl-1,2-dihydroquinoline, 6-dodecyl-2,2,4-trimethyl-1,2-dihydroquinoline, mono- and di-octyliminodibenzyl, polymerised 2,2,4-trimethyl-1,2-dihydroquinoline, octylated diphenylamine, nonylated diphenylamine, N-phenyl-N'-cyclohexyl-p-phenylenediamine, N-phenyl-N'-iso-propyl-p-phenylenediamine, N,N'-di-sec.octyl-p-phenylene-diamine, N-phenyl-N'-sec.octyl-p-phenylenediamine, N,N'-di-(1,4-dimethylpentyl)-p-phenylenediamine, N,N'-dimethyl-N,N'-di-sec.octyl)-p-phenylenediamine, 2,6-dimethyl-4-methoxy-aniline, 4-ethoxy-N-sec.butylaniline, diphenylamine/acetone condensation product and phenothiazine.

2. UV ABSORBERS AND LIGHT STABILISERS 2.1. 2-(4'-Hydroxyphenyl)-benztriazoles such as, for example, the 5'-methyl, 3',5'-di-tert.butyl-, 5'-tert.butyl-, 5'-(1,1,3,3'-tetramethylbutyl)-5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.amyl-derivative.

2.2. 2,4-Bis-(2'-hydroxyphenyl)-6-alkyl-s-triazines such as, for example, the 6-ethyl-, 6-heptadecyl or 6-undecylderivative.

2.3. 2-Hydroxybenzophenones, such as, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy- derivative.

2.4. 1,3-Bis-(2'-hydroxybenzoyl)-benzenes such as, for example, 1,3-bis-(2'-hydroxy-4'-hexyloxy-benzoyl)-benzene, 1,3-bis-(2'-hydroxy-4'-octoxy-benzoyl)-benzene, and 1,3-bis-(2'-hydroxy-4'-dodecyloxy-benzoyl)-benzene.

2.5. Esters of optionally substituted benzoic acids such as, for example, phenylsalicylate, octylphenyl salicylate, dibenzoylresorcinol, bis-(4-tert.butylbenzoyl)-resorcinol, benzoylresorcinol and 3,5-di-tert.butyl-4-hydroxybenzoic acid 2,4-di-tert.butyl-phenyl ester or octadecyl ester or 2-methyl-4,6-di-tert.butylphenyl ester.

2.6. Acrylates such as, for example, α-cyano-β,β-diphenyl-acrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxyvinyl)-2-methyl-indoline.

2.7. Nickel compounds such as, for example nickel complexes of 2,2'-thio-bis-[4-(1,1,3,3-tetramethyl-butyl)-phenol], such as the 1:1 or the 1:2 complex, optionally with additional ligands such as n-butylamine, triethanolamine or N-cyclohexyldiethanolamine, nickel complexes of bis-[2-hydroxy-4-(1,1,3,3-tetramethylbutyl)-phenyl]-sulphone, such as the 2:1 complex, optionally with additional ligands such as 2-ethylcaproic acid, nickel dibutyldithiocarbamate, nickel salts of 4-hydroxy-3,5-di-tert.butylbenzyl-phosphonic acid monoalkyl esters such as of the methyl, ethyl or butyl ester, the nickel complexes of ketoximes such as of 2-hydroxy-4-methyl-phenyl-undecylketoxime, nickel 3,5-di-tert.butyl-4-hydroxy-benzoate and nickel isopropylxanthate.

2.8 Sterically hindered amines such as, for example, 4-benzoloxy-2,2,6,6-tetramethylpiperidine, 4-stearoyloxy-2,2,6,6-tetramethylpiperidine, bis-(2,2,6,6tetramethylpiperidyl)-sebacate, 3-n-octyl-7,7,9,9tetramethyl-1,3,8-triazaspiro[4,5]decane-2,4-dione.

2.9. Oxalic acid diamides such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2', -ethyl-oxanilide, N,N'-bis-(3dimethyaminopropyl)-oxalamide, 2-ethoxy-5-tert.butyl-2'-ethyl-oxanilide and its mixture with 2-ethoxy-2'-ethyl-5,4'-di-tert.butyl-oxanilide, and mixtures of ortho- and para-methoxy-substituted and o- and p-ethoxy-disubsituted oxanilides.

3. Phosphites, such as, for example, triphenylphosphite, diphenylalkylphosphites, phenyldialkylphosphites, tri-(nonylphenyl)-phoshite, trilaurylphosphite, trioctadecylphosphite, 3,9-di-isodecyloxy-2,4,8,10-tetroxa-3,9-diphosphaspiro[5,5]-undecane and tri-(4-hydroxy-3,5-di-tert.butylphenyl)-phosphite.

4. Compounds which destroy peroxides such as, for example, esters of β-thiodipropionic acid, for example the lauryl, stearyl, myristyl or tridecyl esters, mercaptobenzimidazole, or the zinc salt of 2-mercaptobenzimidazole.

5. Basic co-stabilisers such as, for example, alkali metal salts and alkaline earth metal salts of higher fatty acids, for example Ca stearate, Zn stearate, Mg stearate, Na ricinoleate, K palmitate, antimony pyrocatecholate or tin pyrocatecholate.

6. Nucleating agents, such as, for example, 4-tert-butylbenzoic acid, adipic acid and diphenylacetic acid.

7. Other additives such as, for example, lubricants, emulsifiers, fillers, carbon black, asbestos, kaolin, talc, glass fibres, pigments, optical brighteners flameproofing agents, antistatic agents, high pressure additives, detergents, rustproofing agents, anti-foam agents and agents for improving the viscosity.

The manufacture and use of the compounds according to the invention is described in more detail in the examples which follow. In these, parts denote parts by weight, % denotes percentages by weight and °denotes °C.

Example 1

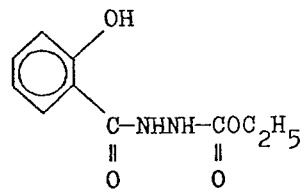

30.4 g. of salicylic acid hydrazide are dissolved in 200 ml of dimethylacetamide and 16 g of pyridine and 22 g of chloroformic acid ethyl ester are then added simultaneously over the course of 30 minutes. Thereafter the reaction mixture is heated to 80°–90° C for 5 hours whilst stirring and is then cooled to room temperature, and about 500 ml of water are added carefully. Hereupon the N-salicyloyl-hydrazine-carboxylic acid ethyl ester produced (Stabiliser No. 1) separates out as a micro-crystalline precipitate. The compound is isolated and is purified by washing with water and recrystallised from ethanol. Melting point 126° C.

If the chloroformic acid ethyl ester in Example 1 is replaced by the equivalent amount of one of the homologous chloroformic acid esters of Table I, whilst otherwise following the same method, the corresponding salicyloylhydrazinecarboxylic acid esters, having the structures and melting points indicated, are obtained as further examples.

Table I

| Example | Cl.COOR | Product | M.p. |
|---|---|---|---|
| 2 | R = C$_8$H$_{17}$(n) | 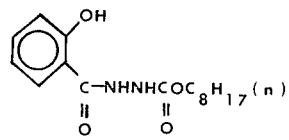<br>Stab. No. 2 | 77°C |
| 3 | R = —CH$_2$—CH$\Big<\substack{C_2H_5 \\ C_4H_9(n)}$ | 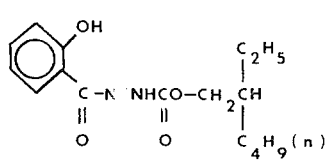<br>Stab. No. 3 | 90°C |

Table I-continued

| Example | Cl.COOR | Product | M.p. |
|---|---|---|---|
| 4 | R = —C₁₈H₃₇(n) | Stab. No. 4 | 103°C |
| 5 | R = —CH₂—⌬ | Stab. No. 5 | 152°C |

EXAMPLE 6

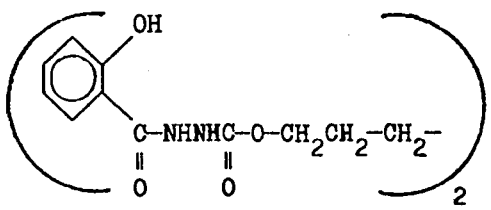

30.4 g of salicylic acid hydrazide are dissolved in 100 ml of dimethylacetamide and 16 g of pyridine and 24.3 g of O,O'-dichlorocarbonylhexanediol are then added simultaneously over the course of 30 minutes.

Thereafter the reaction mixture is heated to 80°C for 3 hours whilst stirring and is then cooled to room temperature, and about 700 ml of water are added carefully. Hereupon, the hexanediol diester of N-salicyloyl-hydrazinecarboxylic acid (Stabiliser No. 6) which has formed precipitates.

The compound is isolated, purified by washing with water and recrystallised from methylcellosolve. Melting point 208° C.

EXAMPLE 7

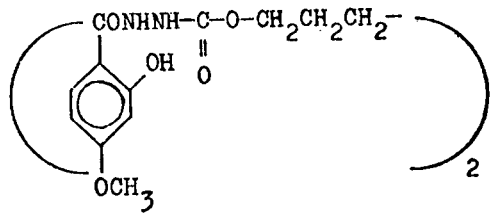

If the salicyclic acid hydrazide in Example 6 is replaced by the equivalent amount of 4-methoxy-2-hydroxybenzoic acid hydrazide and otherwise the same procedure is followed, the hexanediol diester of N-(4-methoxy-2-hydroxy-benzoyl)-hydrazinecarboxylic acid (Stabiliser No. 7) is obtained as a finely crystalline substance of melting point 202° C.

EXAMPLE 8

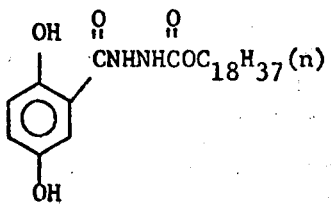

33.6 g of 2,5-dihydroxybenzoic acid hydrazide are dissolved in 150 ml of dimethylacetamide and 66.5 g of chloroformic acid octadecyl ester in 150 ml of dimethylacetamide, and 21 g of triethylamine, are added simultaneously over the course of 30 minutes. Thereafter the reaction mixture is warmed to 40° C for 3 hours whilst stirring, cooled and poured into 2 litres of water. The N-(2,5-dihydroxybenzoyl)-hydrazinecarboxylic acid octadecyl ester obtained (Stabiliser No. 8) forms a pulverulent precipitate which is isolated, washed with water, dried at 80° C and recrystallised from isopropanol. Melting point 163° C.

EXAMPLE 9

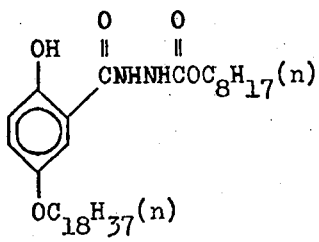

42 g of 5-octadecoxy-2-hydroxybenzoic acid hydrazide are suspended in 200 ml of dimethylacetamide and 8 g of pyridine and 19.3 g of chloroformic acid n-octyl ester are added simultaneously over the course of 30 minutes. The reaction mixture is subsequently heated to 80° C for 5 hours whilst stirring, cooled and poured into 1 litre of water. This produces a white precipitate of the N-(5-octadecoxy-2-hydroxybenzoyl)-hydrazinecarboxylic acid n-octyl ester which has been formed (Stabiliser No. 9). The substance is isolated, washed with water, dried at 60° C and recrystallised from acetonitrile. Melting point 85° C.

EXAMPLE 10

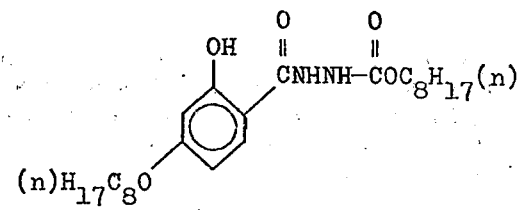

If the acid hydrazide of Example 10 is replaced by an equivalent amount of 4-n-octoxy-2-hydroxybenzoic acid hydrazide and otherwise the same procedure is followed, N-(4-n-octoxy-2-hydroxybenzoyl)-hydrazinecarboxylic acid n-octyl ester (Stabiliser No. 10) is obtained in colourless crystals of melting point 90° C.

EXAMPLE 11

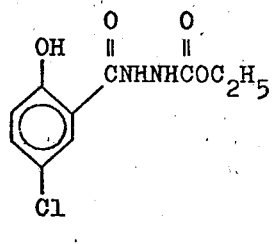

37.2 g of 5-chloro-2-hydroxybenzoic acid hydrazide are dissolved in 200 ml of dimethylacetamide and 16 g of pyridine and 22 g of chloroformic acid ethyl ester are added simultaneously over the course of 30 minutes. The reaction mixture is subsequently heated to 90° C for 3 hours whilst stirring, cooled and poured onto 1 litre of ice water. The precipitate which has separated out slowly crystallises throughout. The N-(5-chloro-2-hydroxybenzoyl)-hydrazinecarboxylic acid ethyl ester thus obtained (Stabiliser No. 11) is isolated, washed with water and recrystallised from ethanol. Melting point 172° C.

EXAMPLE 12

Stabilisation of mineral oil

Test by CERL (Central Electricity Research Laboratories) test:

0.3 g of the Stabiliser No. 3 are dissolved in 300 ml of Shell SETO 27 turbine oil (which has been pre-stabilised with 0.5% of 2,6-di-t-butyl-p-cresol) and the mixture is aerated in a glass apparatus of the type of a gas wash bottle at a temperature of 120° C for 168 hours, by passing air into it. The flow rate is 5 l of air/hour. During this treatment, the oil is in contact with a high gloss-polished strip of sheet copper.

The total acidity developed in the oil is then determined by titration. Futhermore, the amount of insoluble constituents is determined by filtering these off, and is expressed as a percentage by weight of the amount of oil employed. To achieve better separation of the insoluble constituents (sludge), the aerated oil is diluted with an equal volume of toluene. The results are shown in the table which follows.

Table II

| | % by weight of precipitate | Total acidity (mg of KOH/g of oil) |
|---|---|---|
| Experiment without stabiliser | 0.20 | 1.60 |
| Experiment with Stabiliser No. 3 | 0.04 | 0.12 |

EXAMPLE 13

Stabilisation of mineral oil 0.15 g of Stabiliser No. 3 and 0.6 g of copper naphthenate are dissolved in 300 ml of Shell SETO 27 (turbine oil (which has been pre-stabilised with 0.5% of 2,6-di-t-butyl-p-cresol) and the mixture is aerated in a glass apparatus of the type of a gas wash bottle at a temperature of 120° C for 168 hours, by passing air into it. The flow rate is 5 l of air/hour.

The total acidity developed in the oil is then determined by titration. Furthermore, the amount of insoluble constituents is determined by filtering these off, and is expressed as a percentage by weight of the amount of oil employed. To achieve better separation of the insoluble constituents (sludge), the aerated oil is diluted with an equal volume of toluene. The results are shown in the table which follows.

Table III

| | % by weight of precipitate | Total acidity (mg of KOH/g of oil) |
|---|---|---|
| Experiment without stabiliser | 0.24 | 1.39 |
| Experiment with stabiliser | 0.01 | 0.25 |

EXAMPLE 14

Stabilisation of polypropylene a. Production of the test specimens 100 parts of polypropylene (melt index 3.2 g/10 minutes, 230° C/2,160 g) are thoroughly mixed for 10 minutes, in a shaking apparatus, with 0.1 part of 3-(3,5-di-t-butyl-4-hydroxy-phenyl)-propionic acid octadecyl ester, 0.3 part of dilauryl thiodipropionate and 0.5 part of one of the additives listed in Table IV below.

The resulting mixture is kneaded in a Brabender plastograph at 200° C for 10 minutes, 1.0% by weight of copper powder (manufactured electrolytically, Merck) is added and thorough mixing is continued at the same temperature for a further 2 minutes. The mass thus obtained is then pressed in a platen press at 260° C platen temperature to give 1 mm thick sheets from which strips 1 cm wide and 17 cm long are punched with the aid of a punch tool.

The heat-stabilised test specimens without added copper or with added copper but without metal deactivator, which are required for comparison purposes, are manufactured analogously.

b. Test

The effectiveness of the metal deactivators added to the test strips containing copper is tested by heat aging in a circulating air oven at 135° C, in comparison with test strips which do not contain copper. 3 test strips of each formulation are employed. The incipient, easily visible decomposition of the test strips is defined as the end point.

The results are to be found in Table IV below.

Table IV

| Stabiliser No. | Days up to decomposition | |
|---|---|---|
| | Without copper | With copper |
| No additive | 70–95 | 1 |
| 4 | 122 | 65–71 |
| 6 | 88 | 63 |

EXAMPLE 15

Stabilisation of polypropylene a. Production of the test specimens 100 parts of polypropylene (melt index 3.2 g/10 minutes, 230° C/ 2160 g) are thoroughly mixed for 10 minutes, in a shaking apparatus, with 0.1 part of 3-(3,5-di-t-butyl-4-hydroxy-phenyl)-propionic acid octadecyl ester, 0.3 part of dilauryl thiodipropionate and 0.5 part of one of the additives listed in Table V below.

The resulting mixture is kneaded in a Brabender plastograph at 200° C for 10 minutes, 1.0% by weight of copper powder (manufactured electrolytically, Merck) is added and thorough mixing is continued at the same temperature for a further 2 minutes. The mass thus obtained is then pressed in a platen press at 260° C platen temperature to give 1 mm thick sheets from which strips 1 cm wide and 17 cm long are punched with the aid of a punch tool.

The heat-stabilized test specimens without added copper or with added copper but without metal deactivator, which are required for comparison purposes, are manufactured analogously.

b. Test

The effectiveness of the metal deactivators added to the test strips containing copper is tested by heat aging in a circulating air oven at 149° C, in comparison with test strips which do not contain copper. 3 test strips of each formulation are employed. The incipient, easily visible decomposition of the test strips is defined as the end point.

The results are to be found in Table V below.

Table V

| Stabiliser No. | Days up to decomposition | |
|---|---|---|
| | Without copper | With copper |
| No additive | 18–27 | 1 |
| 4 | 13–18 | 13 |
| 6 | 25 | 20 |

What we claim is:

1. Compounds of the formula

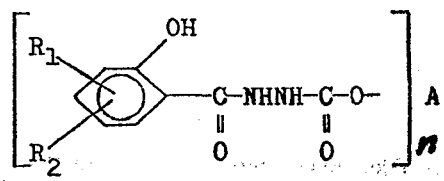

in which $R_1$ denotes hydrogen, alkyl with 1–8 carbon atoms, alkenyl with 3 or 4 carbon atoms, cycloalkyl with 5–8 carbon atoms, aralkyl with 7–9 carbon atoms, phenyl, chlorine, bromine, hydroxyl, alkoxy with 1–18 carbon atoms or acyloxy with 2–18 carbon atoms, $R_2$ denotes hydrogen, alkyl with 1–5 carbon atoms, alkenyl with 3 or 4 carbon atoms, cyclohexyl, aralkyl with 7–9 carbon atoms, chlorine or bromine, $n$ denotes 1 and A denotes alkyl with 3–21 carbon atoms, alkenyl with 3–6 carbon atoms, alkynyl with 3–6 carbon atoms, oxaalkyl with 2–21 carbon atoms, thiaalkyl with 2–21 carbon atoms, the heteroatoms in the oxaalkyl or thiaalkyl radical being separated from one another and/or from the oxygen atom, to which these radicals are bonded, by at least 2 carbon atoms, cyclohexyl or benzyl or $n$ denotes 2 and A denotes alkylene with 2– 10 carbon atoms, alkenylene with 4 carbon atoms, alkynylene with 4 carbon atoms, oxaalkylene with 4–10 carbon atoms or thiaalkylene with 4–10 carbon atoms, the hetero-atoms in the oxaalkylene or thiaalkylene radical being separated from one another and/or from the oxygen atoms, to which these radicals are bonded, by at least 2 carbon atoms.

2. Compounds according to claim 1, in which $R_1$ denotes hydrogen, hydroxyl, chlorine or alkoxy with 1–18 carbon atoms, $R_2$ denotes hydrogen, $n$ denotes 1 and A denotes alkyl with 3–18 carbon atoms, or benzyl, or $n$ denotes 2 and A denotes alkylene with 6 carbon atoms, alkenylene with 4 carbon atoms, alkynylene with 4 carbon atoms, oxaalkylene with 4–10 carbon atoms or thiaalkylene with 4–10 carbon atoms, the hetero-atoms in the oxaalkylene or thiaalkylene radical being separated from one another and/or from the oxygen atoms, to which these radicals are bonded, by at least 2 carbon atoms.

3. Compounds according to claim 1, in which $R_1$ denotes hydrogen, hydroxyl, chlorine or alkoxy with 1–18 carbon atoms, $R_2$ denotes hydrogen, $n$ denotes 1 and A denotes alkyl with 8–18 carbon atoms, or benzyl, or $n$ denotes 2 and A denotes alkylene with 6 carbon atoms.

4. N-Salicyloyl-hydrazinecarboxylic acid (2-ethyl-2-n-butyl)-ethyl ester, as a compound according to claim 1.

5. Organic material which contains, as the stabiliser, compounds of the formula

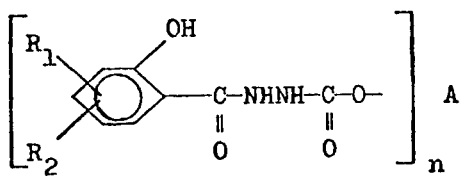

in which $R_1$ denotes hydrogen, alkyl with 1-8 carbon atoms, alkenyl with 3 or 4 carbon atoms, cycloalkyl with 5-8 carbon atoms, aralkyl with 7-9 carbon atoms, phenyl, chlorine, bromine, hydroxyl, alkoxy with 1-18 carbon atoms or acyloxy with 2-18 carbon atoms, $R_2$ denotes hydrogen, alkyl with 1-5 carbon atoms, alkenyl with 3 or 4 carbon atoms, cyclohexyl, aralkyl with 7-9 carbon atoms, chlorine or bromine, $n$ denotes 1 and A denotes alkyl with 1-21 carbon atoms, alkenyl with 3-6 carbon atoms, alkylnyl with 3-6 carbon atoms, oxaalkyl with 2-21 carbon atoms, thiaalkyl with 2-21 carbon atoms, the heteroatoms in the oxaalkyl or thiaalkyl radical being separated from one another and/or from the oxygen atom, to which these radicals are bonded, by at least 2 carbon atoms, cyclohexyl or benzyl or $n$ denotes 2 and A denotes alkylene with 2-10 carbon atoms, alkenylene with 4 carbon atoms, alkynylene with 4 carbon atoms, oxaalkylene with 4-10 carbon atoms or thiaalkylene with 4-10 carbon atoms, the hetero-atoms in the oxaalkylene or thiaalkylene radical being separated from one another and/or from the oxygen atoms, to which these radicals are bonded, by at least 2 carbon atoms.

6. Organic material according to claim 5, characterised in that in the formula $R_1$ denotes hydrogen, hydroxyl, chlorine or alkoxy with 1-18 carbon atoms, $R_2$ denotes hydrogen, $n$ denotes 1 and A denotes alkyl with 2-18 carbon atoms, or benzyl, or $n$ denotes 2 and A denotes alkylene with 6 carbon atoms, alkenylene with 4 carbon atoms, alkynylene with 4 carbon atoms, oxaalkylene with 4-10 carbon atoms or thiaalkylene with 4-10 carbon atoms, the hetero-atoms in the oxaalkylene or thiaalkylene radical being separated from one another and/or from the oxygen atoms, to which these radicals are bonded, by at least 2 carbon atoms.

7. Organic material according to claim 5, characterised in that in the formula $R_1$ denotes hydrogen, hydroxyl, chlorine or alkoxy with 1-18 carbon atoms, $R_2$ denotes hydrogen, $n$ denotes 1 and A denotes alkyl with 8-18 carbon atoms or benzyl, or $n$ denotes 2 and A denotes alkylene with 6 carbon atoms.

* * * * *